(12) United States Patent
Haines et al.

(10) Patent No.: US 8,025,915 B2
(45) Date of Patent: Sep. 27, 2011

(54) METHOD OF PREPARING A MACROMOLECULE DETERRENT SURFACE ON A PHARMACEUTICAL PACKAGE

(75) Inventors: Daniel Haines, Lake Ariel, PA (US); Luis Burzio, Wentzville, MO (US); Matthias Bicker, Mainz (DE); Robert Hormes, Wolfertswil (CH); Horst Koller, Engelburg (CH); Jasmina Buki, St. Gallen (CH); Hartmut Bauch, Weilrod (DE); Manfred Lohmeyer, Nackenheim (DE)

(73) Assignee: Schott AG, Mainz (DE)

( * ) Notice: Subject to any disclaimer, the term of this patent is extended or adjusted under 35 U.S.C. 154(b) by 919 days.

(21) Appl. No.: 11/649,361

(22) Filed: Jan. 4, 2007

(65) Prior Publication Data

US 2007/0187280 A1 Aug. 16, 2007

Related U.S. Application Data

(60) Provisional application No. 60/757,863, filed on Jan. 11, 2006, provisional application No. 60/795,596, filed on Apr. 28, 2006.

(51) Int. Cl.
*A61B 10/00* (2006.01)
*B05D 7/22* (2006.01)
*B29D 22/00* (2006.01)
*B29D 23/00* (2006.01)

(52) U.S. Cl. .......... 427/2.1; 427/230; 427/238; 427/239; 604/403; 604/416; 428/34.1; 428/34.3

(58) Field of Classification Search .......... 427/2.1–2.31, 427/237, 569; 604/403–416
See application file for complete search history.

(56) References Cited

U.S. PATENT DOCUMENTS

| | | | | |
|---|---|---|---|---|
| 4,846,101 A | * | 7/1989 | Montgomery et al. | ... 118/723 E |
| 4,919,889 A | * | 4/1990 | Jones et al. | ...... 422/40 |
| 5,169,720 A | * | 12/1992 | Braatz et al. | ...... 428/423.1 |
| 5,540,984 A | * | 7/1996 | Quincy et al. | ...... 442/118 |
| 6,156,399 A | | 12/2000 | Spallek et al. | |
| 6,267,958 B1 | * | 7/2001 | Andya et al. | ...... 424/130.1 |
| 6,329,024 B1 | * | 12/2001 | Timmons et al. | ...... 427/491 |
| 6,461,334 B1 | * | 10/2002 | Buch-Rasmussen et al. | 604/230 |
| 6,599,594 B1 | * | 7/2003 | Walther et al. | ...... 428/34.6 |
| 7,109,070 B2 | | 9/2006 | Behle et al. | |
| 2009/0155490 A1 | | 6/2009 | Bicker et al. | |

FOREIGN PATENT DOCUMENTS

DE  103 42 401 A1  4/2005

(Continued)

OTHER PUBLICATIONS

Alcantar et al. Polyethylene glycol-coated biocompatible surfaces. Journal of Biomedical Materials Research. vol. 51, Issue 3. Jan. 10, 2000 pp. 343-351.*

(Continued)

*Primary Examiner* — Timothy Meeks
*Assistant Examiner* — Cachet Sellman
(74) *Attorney, Agent, or Firm* — Millen, White, Zelano & Branigan, P.C.

(57) ABSTRACT

A method of preparing a macromolecule deterrent surface on a pharmaceutical package. In particular, the present invention relates to a method of preparing a protein deterrent surface on a pharmaceutical package by applying a coating or coatings directly to the pharmaceutical package that reduces the adsorption of proteins onto pharmaceutical packaging while not affecting the activity of the protein solution contained.

26 Claims, 14 Drawing Sheets

FOREIGN PATENT DOCUMENTS

Figure 1A:
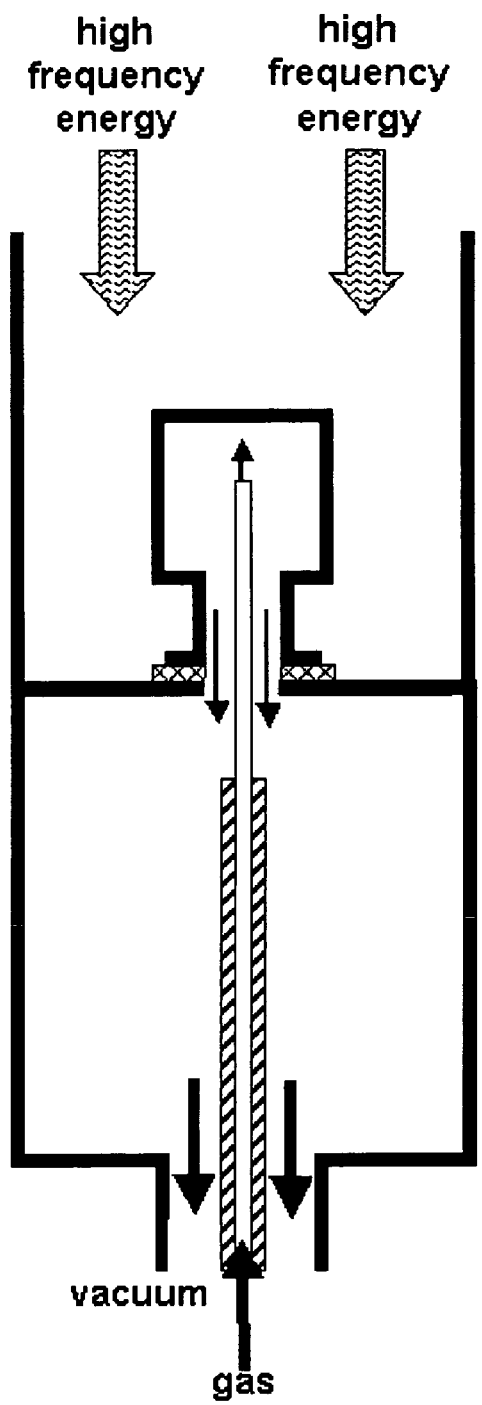

| | | |
|---|---|---|
| DE | 10 2005 040266 A1 | 3/2007 |
| WO | 03/014415 A | 2/2003 |
| WO | 03/082483 A | 10/2003 |

OTHER PUBLICATIONS

Pan et al. Micro-Scale Cell Patterning on Nonfouling PlasmaPolymerized Tetraglyme Coatings by ProteinMicrocontact Printing. Plasmas and Polymers, vol. 7, No. 2, Jun. 2002. pp. 171-183.*

Lopez et al. Glow discharge plasma deposition of tetrethylene glycol dimethyl ether for fouling-resistant biomaterial surfaces. Journal of Biomedical Materials Research. vol. 26 Issue 4. Apr. 1992. pp. 415-439.*

* cited by examiner

| Coating | % Decrease vs Fiolax | # Times >50% Adsorp. Decrease Met vs Fiolax |
|---|---|---|
| TG | 87 | 100 |
| H | 65 | 74 |
| SS | 54 | 63 |
| AMC | 28 | 33 |
| TBF | 21 | 20 |
| Fiolax | 0 | 0 |

Figure 4.

| C1s Peak | C-O Contribution to C1s Peak 286.5 eV (% contribution deconvoluted) |
|---|---|
| Batch 1 Front coating area | 74.5 |
| Batch 1 Middle coating area | 74.8 |
| Batch 1 End coating area | 69.1 |
| Average (Std. Dev.) | 72.8 +/-3.2 |
|  |  |
| Batch 2 Front coating area | 72.3 |
| Batch 2 Middle coating area | 78.1 |
| Batch 2 End coating area | 60.9 |
| Average (Std. Dev.) | 70.4 +/-8.8 |
|  |  |
| Individual Sample 1 | 87.7 |
| Individual Sample 2 | 89.4 |
| Individual Sample 3 | 89.2 |
| Average (Std. Dev.) | 88.9 +/-0.9 |

Figure 10.

METHOD OF PREPARING A MACROMOLECULE DETERRENT SURFACE ON A PHARMACEUTICAL PACKAGE

This application claims the benefit of the filing date of U.S. Provisional Application Ser. No. 60/757,863 filed Jan. 11, 2006 and Ser. No. 60/795,596 and Apr. 28, 2006.

INTRODUCTION

This invention pertains to an improved method of preparing a macromolecule (e.g., protein) deterrent surface on a pharmaceutical package. The coating that deters macromolecular (e.g., protein) adsorption is applied to pharmaceutical packaging materials by plasma chemical vapor deposition. One significant growth area in the pharmaceutical industry is the increasing prevalence of protein based drug formulations. As proteins have a strong affinity for the surface of native packaging materials (e.g., glass, polymers), this results in the loss the active pharmaceutical ingredient by interaction of the protein to the surface leading to permanent immobilization and/or denaturation. For mass produced protein based drugs like insulin the accepted solution is to compensate for the protein loss by overfilling—using a higher than needed concentration and/or volume to provide enough product to passivate the surface and still maintain the required dosage. With the advent of more specialized (expensive) protein based drugs, the increased costs to overfill the packaging container are undesirable both to the manufacturer and consumer.

The adsorption of macromolecules and in particular proteins to a surface depends on a variety of factors: substrate surface chemistry (functional groups present on a native surface or coating thereon), surface figure (flatness, roughness), the structure of the protein (molecular weight, distribution of amino acids, isoelectric point), and the excipients (binders, disintegrants, diluents, suspension and dispersing agents) present in the protein formulations. The chemically heterogeneous structure of proteins allows for surface interaction through hydrogen bonding and a variety of interaction mechanisms (ionic, hydrophobic, Van der Waals forces, entanglement, etc.). To mitigate binding through these mechanisms most protein drug formulators rely on various excipients such as carbohydrates (e.g., trehalose, sucrose), buffers systems (e.g., phosphate, tris, citrate) and surfactants (e.g., polysorbate-80 or polysorbate-20). Though these approaches may be well established they are not always possible for different proteins whose activities may be modified by the addition of excipients resulting in the need for each formulation to be tested for stability of the protein drug contained in the package and the effect of the protein adsorption quantified in terms of loss of protein and protein activity.

Another approach to deter proteins binding to the surface of the package is the application of coatings to the package surface, provided it is feasible in a pharmaceutical packaging scenario (low cost, sterilizable by 1 or more of the accepted methods of autoclaving/EtO exposure/gamma irradiation/electron beam irradiation, non-toxic, 2-3 year stability, 100% coating deposition verifiable, etc.). A large body of literature has established a set of generally accepted theoretical parameters (Ostuni E., Chapman R. G., Holmin R. E., Takayama S., Whitesides G. M. *Langmuir* 2001, 17, 5605-5620) that determine if a surface is likely to deter protein adsorption. In general, a surface that is non-ionic, hydrophilic and hydrogen bond accepting is considered an ideal surface to repel protein adsorption at the liquid/solid interface. The coating should also be sterically hindering to the proteins interaction with the pharmaceutical package and/or component(s) surface (glass, polymer, copolymer, metal, alloys) to avoid not only adsorption, but also denaturation. Other theories have been proposed in the literature to explain the ability of certain coatings to reduce protein adsorption—for instance, see Gombotz et al (Gombotz W. R., Wang G. H., Horbett T. A., Hoffmann A. S. *J. Biomed Mater. Res.* 1991, 12, 1547-1562), who postulate that the effectiveness of a coating (in this case polyethylene oxide) to structure water at the coating/water interface region influences the ability of a coating to reduce protein adsorption.

There is a wealth of general knowledge regarding surfaces and or coatings that resist protein adsorption. A non-exhaustive list include polyethylene oxide/glycol-like and other coatings deposited via plasma assisted chemical vapor deposition that deter protein adsorption—see, for example, Erika E. Johnston E. E., Bryers J. D., Ratner B. D. *Langmuir* 2005, 21, 870-881; Sardella B., Gristina R., Senesi G. S., d'Agostino R., Favia P. *Plasma Process. Polym.* 2004, 1, 63-72; Shen M., Martinson L., Wagner M. S., Castner D. G., Ratner B. D., Horbett T. A. *J. Biomater. Sci. Polymer Edn.* 2002, 13, 367-390; Shen M., Pan Y. V., Wagner M. S., Hauch K. D., Castner D. G., Ratner B. D., Horbett T. A. *J. Biomater. Sci. Polymer Edn.* 2001, 12, 961-978; Ratner B. D., Lopez G. P. U.S. Pat. No. 5,153,072 1992; Lopez G. P., Ratner B. D. *J. Polym. Sci. A—Polym. Chem.* 1992, 30, 2415-2425; Ratner B. D., Lopez G. P. U.S. Pat. No. 5,002,794 1991. For (derivatized) alkanethiol coatings deposited that deter protein adsorption see, for example, Li L. Y., Chen S. F., Ratner B. D., Jiang S. Y. *J. Phys. Chem. B* 2005, 104, 2934-2941; Chirakul P., Pérez-Luna V. H., Owen H., López G. P. *Langmuir* 2002, 18, 4324-4330; Prime K. L., Whitesides G. M. *J. Am. Chem. Soc.* 1993, 115, 10714-10721; Pale-Grosdemange C., Simon E. S., Prime K. L., Whitesides G. M. *J. Am. Chem. Soc.* 1991, 113, 12-20. For organosilane coatings that deter protein adsorption see, for example, Seigers C., Biesalski M., Haag R. *Chem. Eur. J.* 2004, 10, 2831-2838; Sunder A., Mulhaupt R. United States Patent Application 2003/0092879 2003; Yang Z., Galloway J. A., Yu H. *Langmuir* 1999, 15, 8405-8411; Lee S. W., Laibinis P. E. *Biomaterials* 1998, 19, 1660-1675; Lee S. W., Laibinis P. E. U.S. Pat. No. 6,235,340 2001. For hydrogel (H) coatings that deter protein adsorption see, for example, Mao G., Metzger S. W., Lochhead M. J. U.S. Pat. No. 6,844,028 2005. For poly-L-lysine/polyethylene glycol coatings that deter protein adsorption see, for example, Hubbel J. A., Textor M., Elbert D. L., Finken S., Hofer R., Spencer N. D., Ruiz-Taylor L. United States Patent Application 2002/0128234 2002; Huang N. P., Michel R., Voros J., Textor M., Hofer R., Rossi A., Elbert D. L., Hubbell J. A., Spencer N. D. *Langmuir* 2001, 17, 489-498; Kenausis G. L. Vörös J., Elbert D. L., Huang N., Hofer R., Ruiz-Taylor L., Textor M., Hubbell J. A., Spencer N. D. *J. Phys. Chem. B* 2000, 104, 3298-3309. For polyethylene oxide graft coatings see, for example, Sofia S. J., Premnath. V., Merrill E. W. *Macromolecules* 1998, 31, 5059-5070. These examples represent but are not an exhaustive compilation of the large number of available surface treatment and/or coating possibilities.

Currently, no commercially available pharmaceutical package (native or coated) contains all of the favorable characteristics described above, but tends to have a few desirable ones while still having some that promote protein adsorption. While glass (borosilicate, soda-lime, etc.) is hydrophilic and hydrogen bond accepting, it is highly ionic and has no steric hindrance to deter protein binding. The high density of negative charges under liquid formulation conditions (pH 5-9) on the surface will promote the ionic binding of positively charged residues on the proteins (i.e. lysine, histidine, and the amino terminus). The siliconization of glass to passivate the surface and provide lubricity in syringes results in a relatively non-ionic surface that is sterically blocked, but the silicone oil renders the surface very hydrophobic while decreasing its hydrogen bond accepting ability. Hydrophobic surfaces tend to exclude water and facilitate the adsorption of proteins. The hydrophobicity of the environment the proteins encounter can also lead to protein denaturation as the hydrophobic core of the proteins seeks to interact with the surface and unfold its native structure to obtain a minimum free energy conformation. Hydrophobic coatings containing fluorine with anti-adherency properties for solutions/suspensions containing medicinally relevant particles/agglomerates have been prepared previously by plasma enhanced chemical vapor deposition—see, for example, Walther M., Geiger A., Auchter-Krummel P., Spalleck M. U.S. Pat. No. 6,599,594 2003.

Therefore, glass and polymeric surfaces would certainly benefit from a coating that would contain all of the desirable characteristics and would deter macromolecule and in particular protein binding. Surfaces susceptible to macromolecule (e.g., protein) adsorption include pharmaceutical packaging components (e.g., glass vials, ampoules, stoppers, caps, ready to fill glass and plastic syringes, cartridge-based syringes, pure silica-surfaced vials, plastic-coated glass vials, plastic and glass storage bottles, pouches, pumps, sprayers and pharmaceutical containers of all types) and medical devices (e.g., catheters, stents, implants, syringes etc). Any candidate surface considered for contact with a protein and is susceptible to protein adsorption can be coated to reduce the amount of bound protein. Many polymer coatings have been designed with the theoretical considerations described above in mind, but there has not been a solution to the problem for pharmaceutical packages and the rigors that must be met for the coating to be utilized along with protein drugs. The results obtained on gold coated substrates (Ostuni E., Yan L., Whitesides G. M. *Colloids Surfaces B: Biointerfaces* 1999, 15, 3-30) with self-assembled monolayer coatings elucidating the characteristics that make a coating effective at reducing protein adsorption (Pertsin A. J., Grunze M., Garbuzova I. A. *J. Phys. Chem B* 1998, 102, 4918-4926; Seigel R. R., Harder P., Dahint R., Grunze M., Josse F., Mrksich M., Whitesides G. M. *Anal. Chem.* 1997, 69, 3321-3328) have little practical application to the realities of pharmaceutical packages due to cost of such a surface. The real-life applications are with pharmaceutically relevant surfaces that are coated (e.g. glass, rubber, elastomers, plastics, and other polymers) and then tested exposed/filled with proteins that are possible drug candidates or already established drugs (e.g., immunoglobulins, insulin, erythropoietin, etc.).

FIGS. 1a, 1b, 1c, and 2 depict methods of the present invention. To produce coatings acceptable under the national regulatory agency regulations (FDA, USP, EP, JP) there is the requirement to manufacture coatings that can be 100% verifiable for quality—current methods of plasma assisted chemical vapor deposition coating via batch reactors cannot yet achieve the coating reproducibility required in a cost effective manner nor can they be verified in a cost effective manner. Barrier coatings, such as $SiO_2$, to reduce ion exchange between substrate and solution and to reduce the exposure of packaged solutions to various gases, have been successfully applied to the standards required by pharmaceutical packaging governing agencies via plasma enhanced chemical vapor deposition methods—see for example (DE 196 29 877 M. Walther et al.; EP 08 210 79 M Walther et al.; DE 44 38 359 M. Walther et al.; EP 07 094 85 M. Walther et al.; DE 296 09 958 M. Walther et al.). U.S. Pat. No. 6,599,594 discloses coatings comprising Si, O, C, and H; coatings comprising Si, O, C, H, F; HMDSO (hexamethyldisiloxane) coatings; $C_6F_{10}$ $(CF_3)_2$ coatings; and $C_6F_6$ coatings. These coatings are known from the literature to slightly reduce the adsorption of certain proteins but not to fully deter protein adsorption or prevent protein denaturation. See, for instance, Fang F., Szleifer I. *Biophys J* 2001 80 2568-2589 (adsorption of albumin and IgG from serum). U.S. Pat. No. 5,900,285 discloses HMDSO (containing Si, C, H, O); polyethylene, parylene, polybutene, polypropylene, polystyrene (containing C, H); phthalocyanine (containing C, H, N), and various, mainly hydrocarbon containing, molecules for use as barrier coatings. While the barrier coatings act to protect the formulations inside of a pharmaceutical package against diffusing species such as water vapor, carbon dioxide, oxygen, etc. and from ion exchange with the packaging material, they are generally not effective at deterring protein adsorption or preventing protein denaturation.

However, coating precursors, specifically organic (ethers, esters) precursors that reduce protein adsorption having the aforementioned properties when used as a coating deposited via plasma assisted chemical vapor deposition, have not been successfully applied to pharmaceutical packages due to the technical issues (precursor chemical and temperature stability, low power deposition, reproducibility of coating properties, uniformity of coatings, etc.) associated with their deposition.

SUMMARY OF THE INVENTION

The present invention relates to a method of preparing a macromolecule deterrent surface on a pharmaceutical package (or synonymously, a pharmaceutical container) by depositing a coating that deters macromolecule adsorption directly onto the surface of a pharmaceutical package by plasma chemical vapor deposition. The pharmaceutical package acts as the reaction chamber thus creating a uniform coating. Various pharmaceutical packages and components thereof such as vials, plastic-coated vials, syringes, plastic coated syringes, ampoules, plastic coated ampoules, cartridges, bottles, plastic coated bottles, pouches, pumps, sprayers, stoppers, plungers, caps, stents, lids, needles, catheters or implants can be coated according to the method of the present invention. Any pharmaceutical package that comes in contact with a pharmaceutical or biotechnological substance or formulation is contemplated. Pharmaceutical packaging substrates made from glass (e.g., Type 1, a silicate, a borate, a borosilicate, a phosphate, a soda-lime silicate, Type 2, Type 3, and colored versions thereof to protect formulations from various forms of electromagnetic radiation), chemically treated glass (e.g., to decrease surface and near surface alkali content or to increase the strength of the glass), acrylic, polycarbonate, polyester, polypropylene, polyacetal, polystyrene, polyamide, polyacrylamide, polyimide, polyolefin, cyclic olefin copolymers (e.g. Topas™-COC), rubber, elastomers, a thermosetting polymer, a thermoplastic polymer, metals, or alloys are contemplated. In particular, pharmaceutical packaging materials that have a siliconized or silanized surface are useful as are pharmaceutical packaging materials that have a coating which lowers the surface energy by $\geq 5$ dynes/cm relative to the uncoated pharmaceutical package (e.g. silicone oils and hydrophobic coatings that aid in emptying out the container). Also useful are pharmaceutical packaging materials that have a barrier coating to reduce ion exchange, leachables, extractables, oxygen permeation, oxygen migration, water migration, water permeation, carbon dioxide permeation, and electromagnetic radiation transmission.

In comparison to uncoated pharmaceutical package substrates the substrates prepared by the method of the invention reduce the adsorption of macromolecules to the surface by more than 25%. Preferred coatings reduce the adsorption of macromolecules to the surface by more than 50% and particularly preferred coatings reduce the adsorption of macromolecules to the surface by more than 75%. Macromolecules that are deterred include naturally occurring or synthetically prepared biomolecules or a derivative thereof (e.g., nucleic acid, polynucleotide, protein, carbohydrate, or protein/nucleic acid complex) in solution or solid state.

The coating precursors can be from any chemical family. Preferred families are ethers, esters, silanes, oxides, and functionalized derivatives thereof. Most preferably the coatings of use in the present invention may be prepared from one or more chemical precursors such as, for example, an ether monomer or ester monomer or functionalized derivatives thereof, which contains one or more halogen, alkyl, vinyl, alkynyl, aromatic, hydroxylic, acid, carbonyl, aldehyde, ketone, amine, amino, amide, nitro or sulfonyl derivatized functional groups. Particularly preferred coating precursors are polyethers (e.g., diglyme, a triglyme, a tetraglyme, a pentaglyme, a hexaglyme, or functionalized derivatives thereof). Excellent reduction in macromolecule adsorption to pharmaceutical packages can be achieved with tetraethylene glycol dimethyl ether (TG). Suitable precursors may be deposited either simultaneously or in sequence. Additionally they may be applied over an existing coating such as a first inorganic oxide layer (e.g., $SiO_2$, $TiO_2$, $ZrO_2$ or $Al_2O_3$), a first adhesion layer, or a barrier layer. Suitable precursors are the compounds disclosed in DE 196 29 877; EP 08 210 79; DE 44 38 359; EP 07 094 85 and DE 296 09 958, which are incorporated by reference herein.

BRIEF DESCRIPTIONS OF THE DRAWINGS

Various features and attendant advantages of the present invention will be more fully appreciated as the same becomes better understood when considered in conjunction with the accompanying drawings, in which like reference characters designate the same or similar parts throughout the several views, and wherein:

FIG. 1a: Schematic diagram of a preferred plasma assisted chemical vapor deposition system using the pharmaceutical article (vial or syringe) as the coating chamber.

Figure 1B:
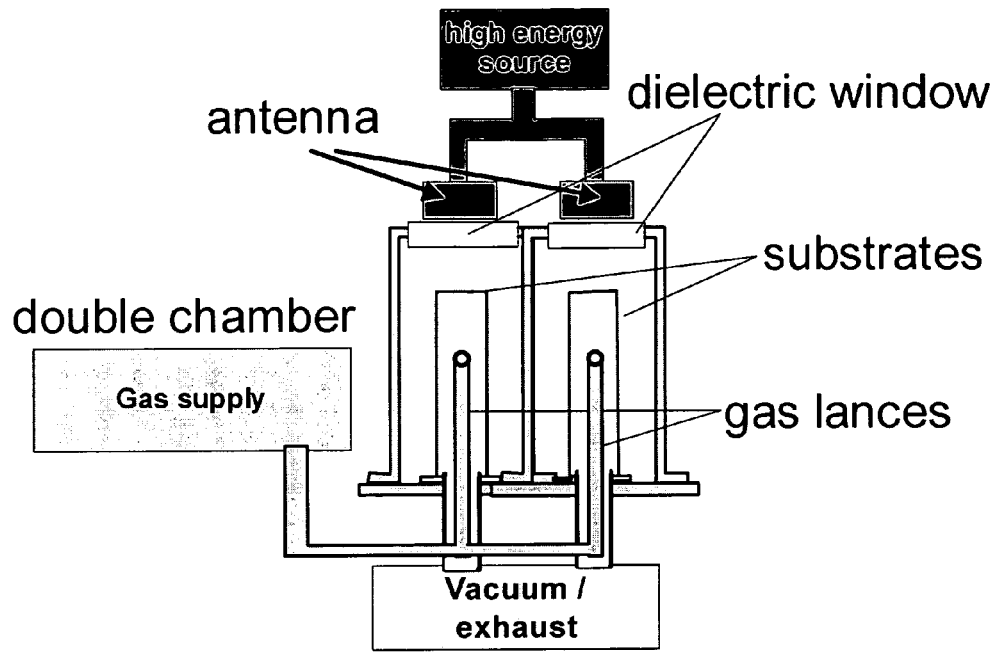

FIG. 1b: Schematic diagram of one preferred plasma assisted chemical vapor deposition system using a double chamber reactor whereby the pharmaceutical article (vial or syringe) is used as a coating chamber. High frequency energy (preferably microwave energy with 2.45 GHz) is split into two parts and coupled into the reaction chamber by separate antennas.

Figure 1C:
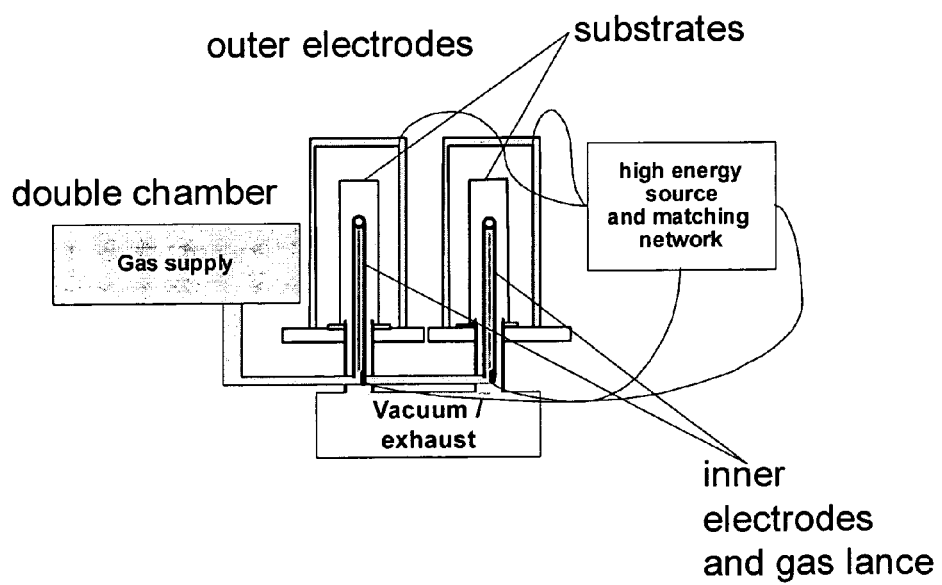

FIG. 1c: Schematic diagram of one preferred plasma assisted chemical vapor deposition system using a double chamber reactor whereby the pharmaceutical article (vial or syringe) is used as a coating chamber. High frequency energy (preferably radio frequency energy with 13.56 MHz is coupled into the two reaction chambers using separate outer and inner electrodes for each chamber. The gas lances are used as inner electrodes.

Figure 2:
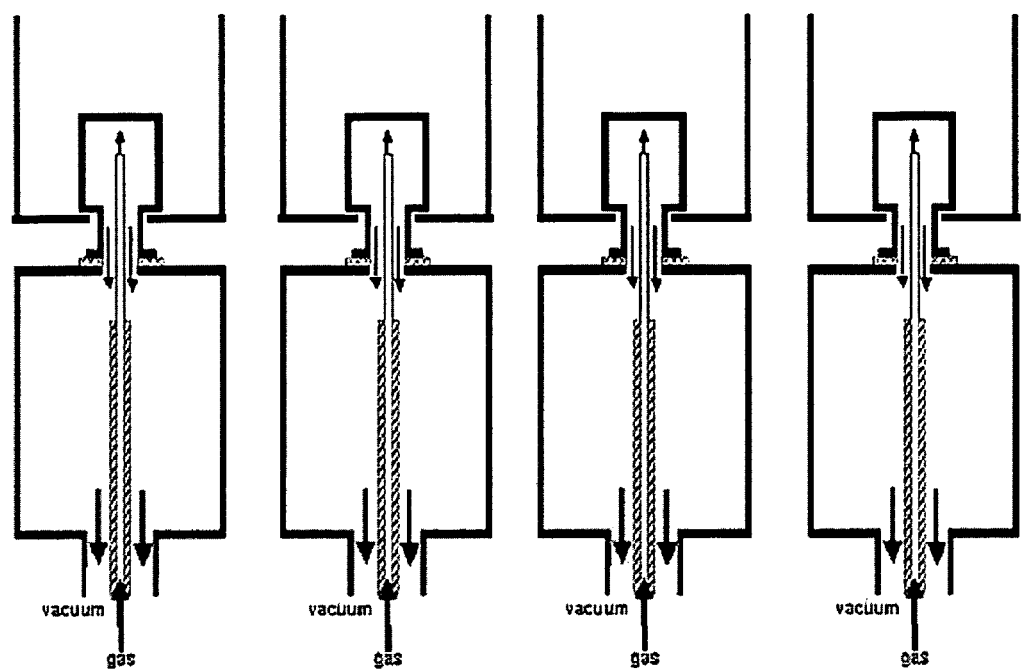

FIG. 2: Schematic diagram of a plasma assisted chemical vapor deposition system with multiple stations for coating multiple individual articles simultaneously.

Figure 3:
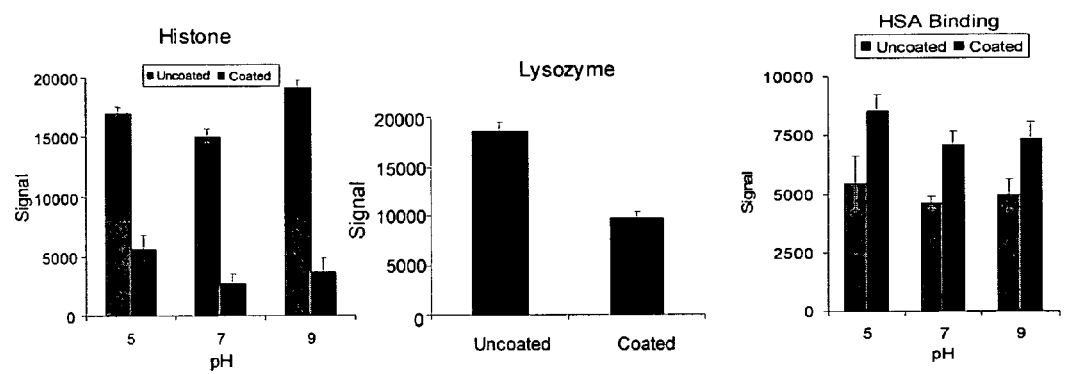

FIG. 3: The effect of changing the surface charge to affect the binding of positively and negatively charged proteins {histone, lysozyme (positive) and human serum albumin (HSA—negative)}. The proteins are labeled with a fluorescent dye (Cyanine-3) and then incubated on uncoated and aminosilanized Type 1 formulated glass slide surfaces. The signal is a direct indication of the amount of protein adsorbed to the surface.

FIG. 4: Reduction of protein adsorption on uncoated and various coated Type 1 formulated glass slides. The table describes the results with respect to the Fiolax control. The "% decrease vs. Fiolax" refers to the % less of protein adsorption observed with respect to Fiolax. The column marked "#>50% Adsorp. Decrease Met vs Fiolax" refers to the % of time that the reduction in protein adsorption is reduced by at least 50% with respect to Fiolax. This is a percentage of 15 samples (5 proteins in three different formulations).

Figure 5:
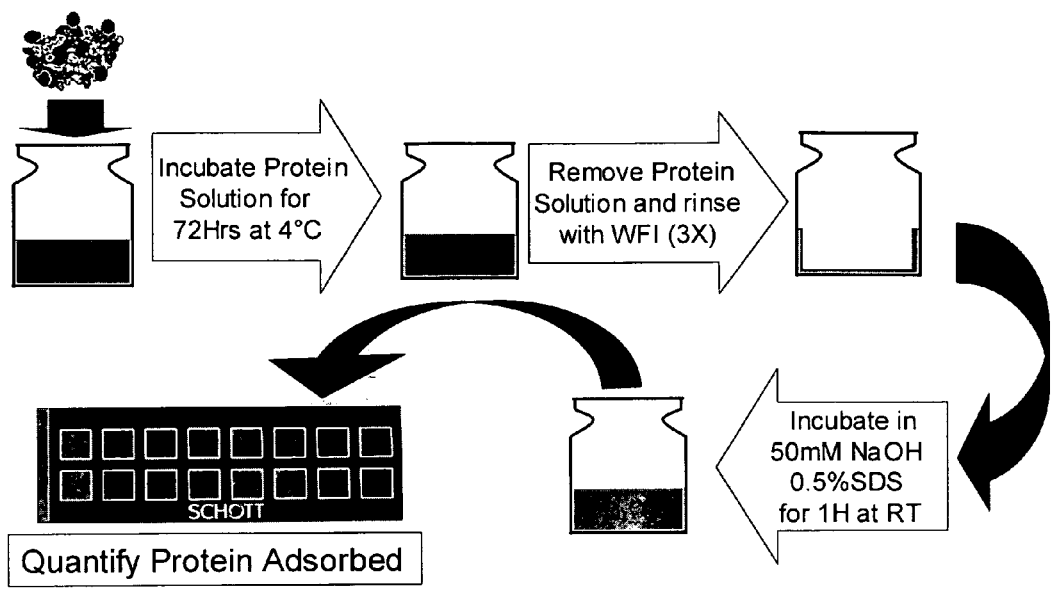

FIG. 5: Description of method used to analyze the adsorption of proteins to pharmaceutical packaging (PP) surface. The method is based on removing the protein that is adsorbed to the surface by washing with 50 mM NaOH/0.5% SDS. This solution removes more than 90% of the protein adsorbed onto glass slides.

Figure 6:
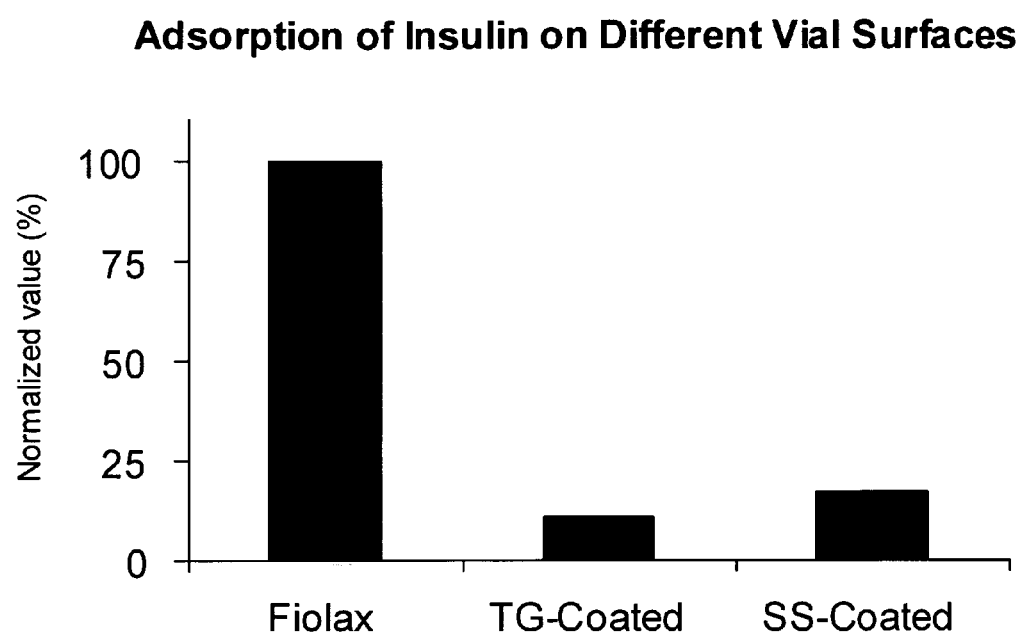

FIG. 6: Adsorption of insulin to coated tetraglyme (TG) and poly-l-lysine/polyethylene glycol (SS) and uncoated vials (Fiolax). The vials are incubated with the protein solution and the adsorption is determined using the method described in Example 1.

Figure 7:
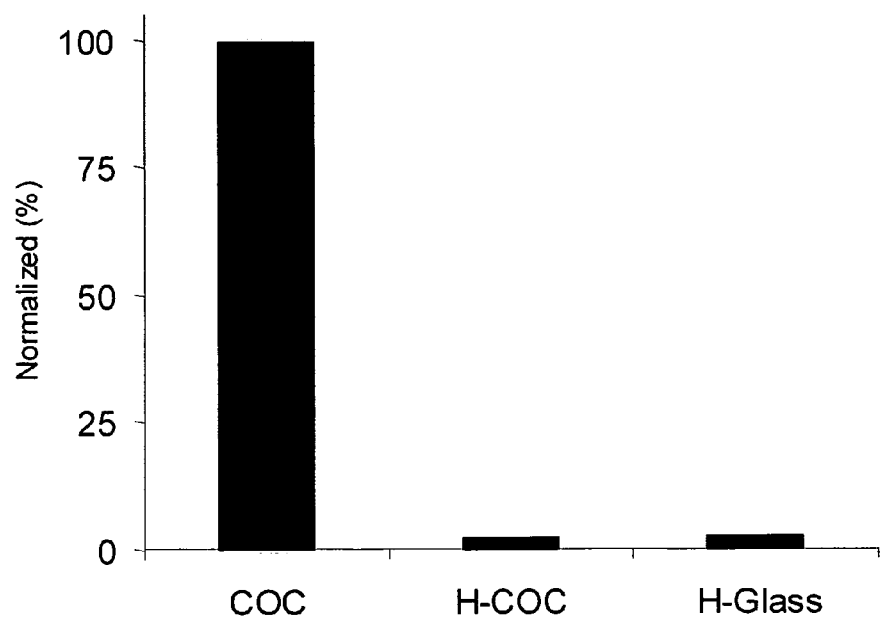

FIG. 7: Adsorption of insulin to hydrogel (H) coated syringes. Glass and Topas™ polymer syringes (COC copolymer made from norbornene and ethylene) are coated with the H coating and the amount of protein adsorbed is measured using the method described in Example 1.

Figure 8:
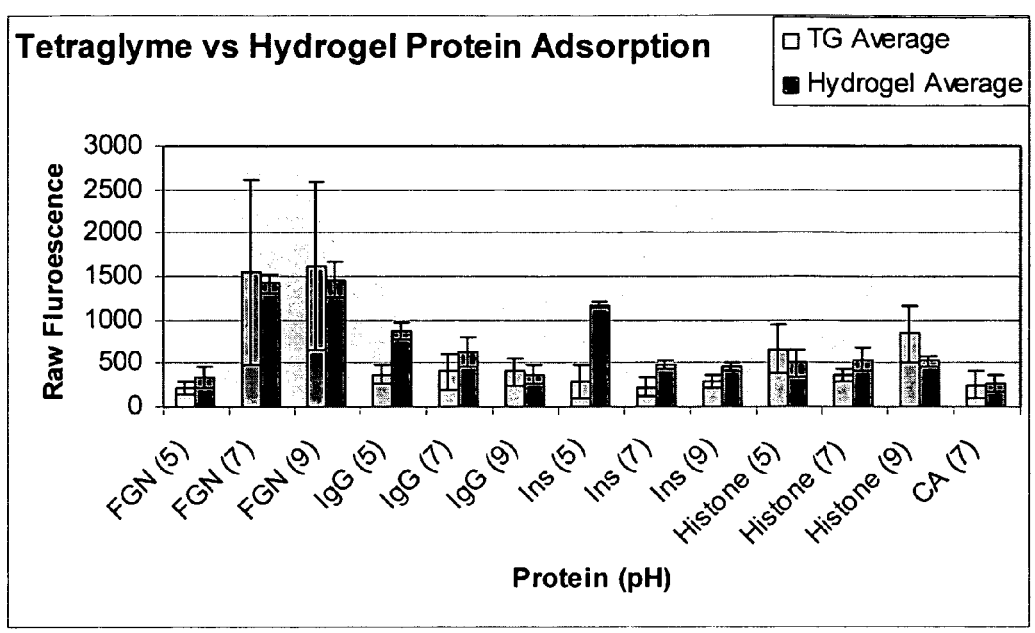

FIG. 8: Comparison of the adsorption of fluorescently labeled fibrinogen, IgG, insulin, histone, and carbonic anhydrase at pH 5, 7, 9 for H and TG coated surfaces.

Figure 9:
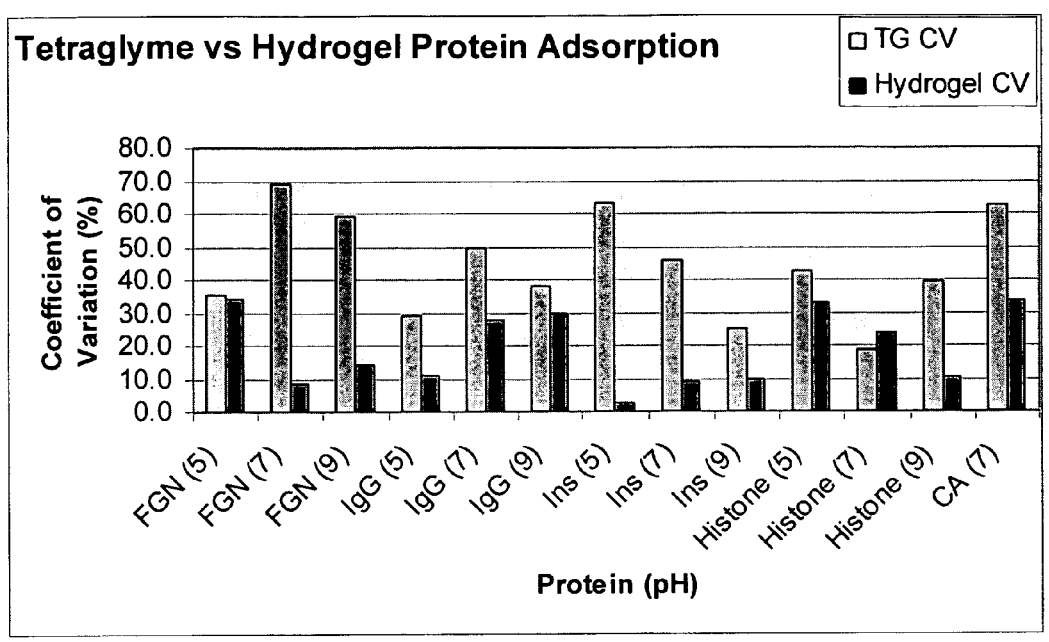

FIG. 9: Comparison of the coefficient of variation of fluorescently labeled fibrinogen, IgG, insulin, histone, and carbonic anhydrase at pH 5, 7, 9 for H and TG coated surfaces.

FIG. 10: Table of % C/O from deconvoluted photoelectron C1s spectra from two batch processes and three individual coatings using the article as the reactor showing the higher % contribution of C/O and reduced variation using the article as the reactor.

Figure 11:
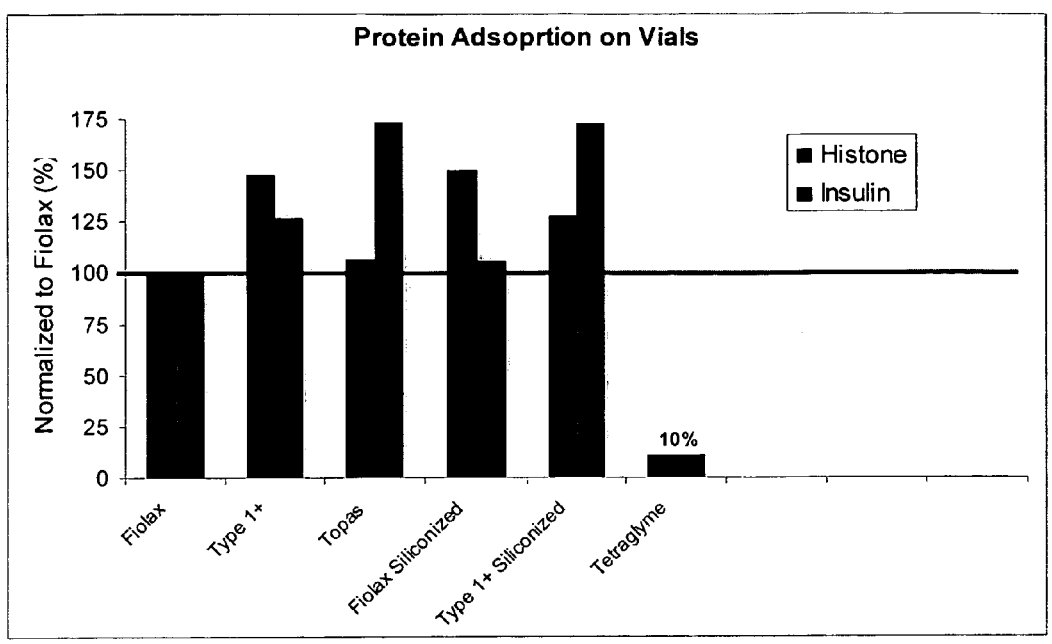

FIG. 11: Compares protein (histone and insulin) adsorption onto vials having various surfaces. As can be seen compared to the Type 1+ surface (Type 1 glass with barrier coating), TG reduces the adsorption of protein by 90%.

Figure 12:
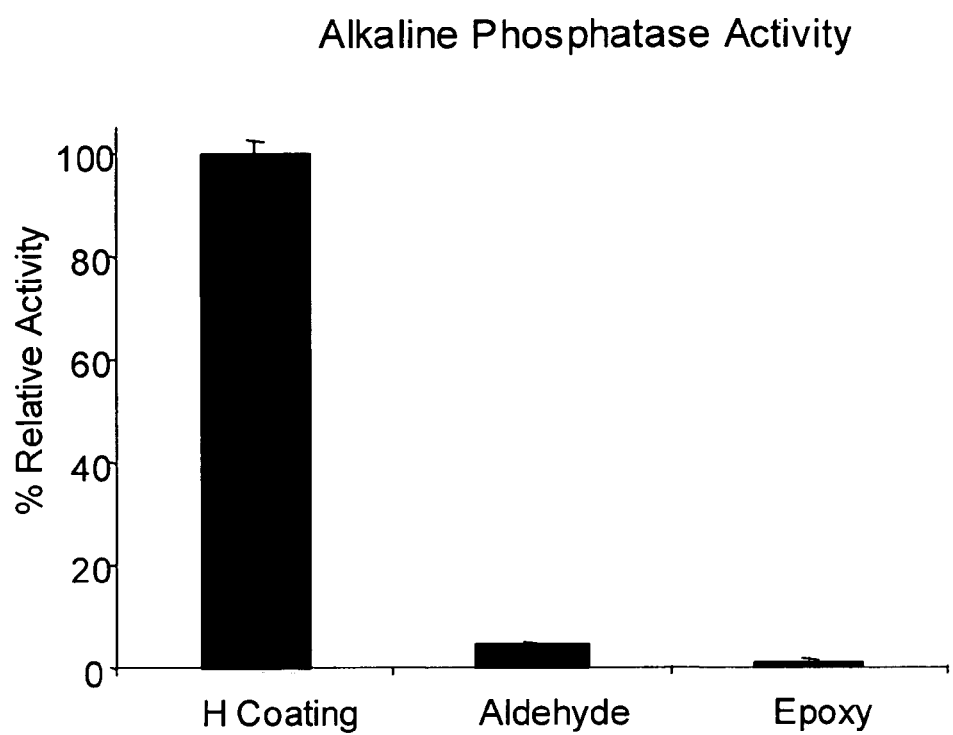

FIG. 12. Depicts the activity of alkaline phosphatase after adsorption to different coated Type 1 glass slides.

Figure 13:
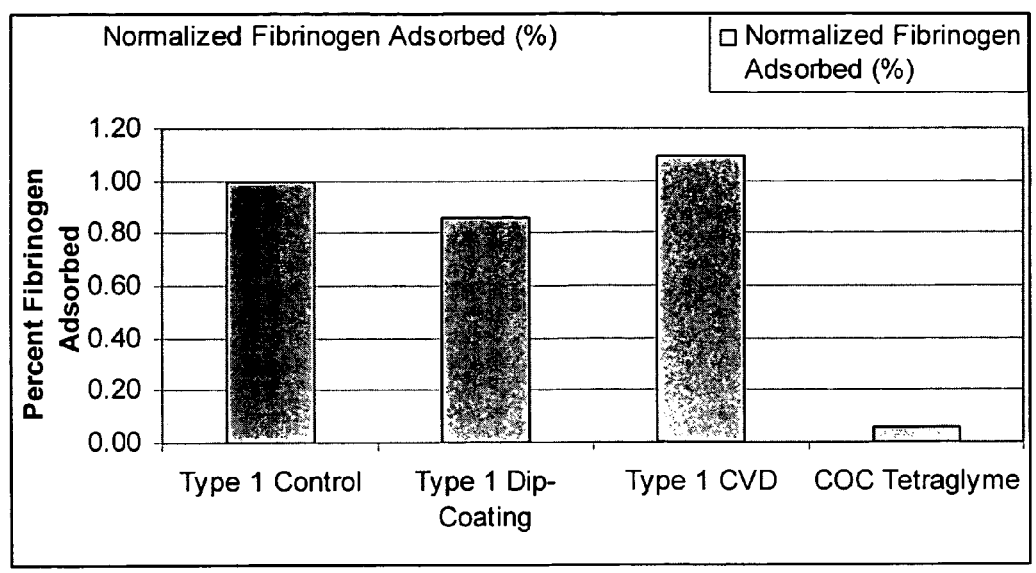

FIG. 13. Compares fibrinogen adsorption on slides coated with tetraglyme deposited via a plasma-assisted process vs. slides coated with tetraglyme deposited via dip-coating or chemical vapor deposition methods.

DETAILED DESCRIPTION OF THE INVENTION

The term "pharmaceutical package" as used herein means any container or medical device or component(s) thereof that comes in contact with a pharmaceutical, biological or biotechnological substance or formulation in solution or solid state. Examples include vials, plastic-coated vials, syringes, plastic coated syringes, ampoules, plastic coated ampoules, cartridges, bottles, plastic coated bottles, pouches, pumps, sprayers, stoppers, plungers, caps, lids, needles, catheters, stents, implants, and components thereof which come in contact with macromolecules.

The term "macromolecule" as used herein means naturally occurring or synthetically prepared biomolecules or derivatives thereof such as, for example, nucleic acids, polynucleotides, proteins, peptides, antibodies, carbohydrates, protein/nucleic acid complexes, in solution or solid state.

The term "protein solution" refers to a particular protein of interest in the presence of (typically) an aqueous solution that may contain various additives, which can also have an effect on the adsorption of the proteins to the surface. Typical protein solutions to be tested include pharmaceutically relevant moieties such as cells, tissues, and derivatives thereof. Among the proteins are included any polyaminoacid chain, peptides, protein fragments and different types of proteins (e.g., structural, membrane, enzymes, antigens, monoclonal antibodies; polyclonal antibodies, ligands, receptors) produced naturally or recombinantly, as well as the derivatives of these compounds, etc. Specific protein drugs include antibodies (e.g. Remicade and ReoPro from Centocor; Herceptin from Genentech; Mylotarg from Wyeth, Synagis from MedImmune), enzymes (e.g. Pulmozyme from Genentech; Cerezyme from Genzyme), recombinant hormones (e.g., Protropin from Genentech, Novolin from Zymogenetics, Humulin from Lilly), recombinant interferon (e.g., Actimmune from InterMune Pharmaceutical; Avonex from BiogenIdec, Betaseron from Chiron; Infergen from Amgen; Intron A from Schering-Plough; Roferon from Hoffman-La Roche), recombinant blood clotting cascade factors (e.g., TNKase from Genentech; Retavase from Centocor; Refacto from Genetics Institute; Kogenate from Bayer) and recombinant erythropoietin (e.g., Epogen from Amgen; Procrit from J&J), and vaccines (e.g., Engerix-B from GSK; Recombivax HB from Merck & Co.).

The term "plasma chemical vapor deposition" as used herein encompasses assisted, enhanced, impulse or continuous chemical vapor deposition and variations thereof (in the literature assisted and enhanced are sometimes used interchangeably). Assisted plasma CVD means the desired coating requires plasma to achieve the required properties or processing considerations with respect to its CVD produced counterpart. A coating can be deposited via CVD but the coating process (rate, uniformity, thickness, etc.) and or properties (morphology, macromolecule deterrence, etc.) are enhanced using plasma. Plasmas are useful in coating processes when generation of charged reactive species and their transport to substrates for participation in the coating formation are important parameters. In impulse plasma CVD the energy is supplied in a non-continuous fashion whereas in continuous plasma CVD the energy is continuous.

As used herein the term "reaction chamber" means the pharmaceutical package, as discussed above, acts as the coating chamber. The precursor gas is applied directly into the pharmaceutical container and electromagnetic radiation is applied generating a plasma. The resulting reaction creates a coating on the surface of the pharmaceutical package that will come in contact with macromolecules. For example, see FIGS. 1a-1c and 2.

This invention pertains to an improved method of manufacture and deposition of coatings to deter macromolecule (e.g. protein) adsorption to pharmaceutical packaging materials by plasma chemical vapor deposition. The current state of the art for depositing coatings that reduce protein adsorption via plasma assisted chemical vapor deposition is described for radio-frequency power sources using barrel type (Ratner B. D. et al. U.S. Pat. No. 5,002,794; Ratner B. D. et al. U.S. Pat. No. 5,153,072) and parallel plate (Sardella E. et al *Plasma Process. Polym.* 2004, 1, 63-72) designs. These reactors enable small batch production with limited substrate size and control over coating uniformity. For application in the pharmaceutical packaging industry, products have to be produced with processes that are highly controlled and verifiably reproducible; pharmaceutical packaging products are typically required by the respective national pharmacopeias (USP/EP/JP) and/or pharmaceutical manufacturers to go through 100% quality control of the packaging container production process. The current designs and resulting process coating methodology need to be improved to reproducibly manufacture coated articles to these standards while enabling higher volume production of a variety of substrate dimensions.

This invention is a fundamental change in reactor design and process methodology to the current state of the art. The invention utilizes the pharmaceutical package and/or component(s) thereof (e.g. vial, syringe, ampoule, bottle, piston, needle, cap etc.) as the reaction chamber. By using the substrate as the reaction chamber a higher degree of control over the applied coating can be achieved compared to a batch type process in which a larger reaction chamber is utilized. Systems of these types have been successfully built and used in the food and pharmaceutical industries to deposit $SiO_2$ barrier coatings (oxygen barriers). A pictorial description of a preferred embodiment is shown in FIGS. 1a-1c. The pharmaceutical package (and/or components thereof) is brought into contact with a structure (in one preferred embodiment the structure is a flat-bottom U-shaped structure; see FIG. 1a). The package is sealed to the flat-bottom U-shaped structure and sealed via a vacuum pump system. In a first step the package is evacuated only inside by a vacuum pump. In a next step, after opening valves, the process gas containing the precursor(s) flows through a gas channel (e.g. a gas lance) into the chamber and it is pumped continuously by a vacuum pump. High frequency energy (e.g. radio frequency, microwave frequency with pulsed energy) is coupled into the package and used to ignite plasma inside the container. During the plasma coating process the light emission of the plasma and other process parameters like pressure, gas flow, and temperature are monitored. After depositing the coating layer onto the internal container surface the connection to the vacuum pump and to the gas source is interrupted by valves and the input of high frequency energy is stopped. The package is vented to atmospheric pressure and leaves the structure afterwards. A preferred method includes one or more additional steps prior to the process gas being introduced. These additional steps include the introduction of a carrier gas (i.e. argon, nitrogen, oxygen, helium, neon, etc.) to the chamber and ignition of a plasma for surface chemistry modification, removal of contaminants (i.e. adventitious carbon), sterilization, and/or heating of the chamber. In a preferred embodiment multiple stations are used to coat multiple individual articles simultaneously (FIG. 3).

There are several improvements obtained using the substrate as the reaction chamber over batch type reactors. Process times can be shortened due to smaller area to be coated (one substrate vs. many) and lower volumes of precursors are required. Coating uniformity is improved by having a stable, reproducible plasma field over the coating area. The plasma field required for one substrate is smaller (i.e. easier to make, more uniform and stable) and more cost effective to generate than a plasma field required for a larger area that coats many substrates simultaneously. Good coating uniformities can especially be realized on 3-dimensional substrates by using a pulsed plasma process leading to a good gas exchange during the interruption of the plasma ignition. 100% verification of coating deposition is easier and more cost effective to achieve using the substrate as the reaction chamber compared to substrates prepared in a plasma assisted chemical vapor deposition batch process. For this 100% quality inspection the light emission of the plasma, the process pressure, the coating temperature and gas flow can be controlled and verified for each coated container. Furthermore, another important advantage of using the pharmaceutical package as a coating reactor is that no contamination of the surface occurs whereas contamination from particulates occurs in many batch reactors. Thus, the method of the present invention avoids the problem of particles falling into the package and maintenance work for cleaning the reactor chamber is eliminated. An additional advantage of this method is the use of a positive temperature gradient, which helps to limit and/or avoid condensation of the coating onto the article surface.

This method is applicable to all electromagnetic energy sources. Preferred frequencies are high frequencies, mainly 40 kHz, 13.56 MHz, 2.45 GHz. This method is applicable to all pharmaceutical packaging components (e.g., vials, syringes, ampoules, plungers, stoppers, needles, gaskets etc.) and their materials (e.g., glass, elastomer, polymer, metal, alloys, etc.). The pharmaceutical package material can be any glass, polymer, copolymer, metal, or alloy. Preferred materials are borosilicate (FIOLAX™, SUPRAX™, and DURAN™) and soda lime glasses, Topas COC™ resins (cyclic olefin copolymer made from ethylene and norborene), iron/titanium/aluminum and alloys thereof, rubber, silicone, and silanized or siliconized coated materials thereof. Exemplary borosilicate glass compositions are disclosed in W. Kiefer U.S. Pat. No. 4,870,034 1989 and E. Watzke et al U.S. Pat. No. 5,599,753 1997. Another form of preferred materials are thermoplastic polymer coated versions of the aforementioned container materials (PURGARD™).

The coating precursors may be from any chemical family. Preferably, the coating will be universal, and as such deter the adsorption of all potential proteins formulations. In some instances, this will not be the case and an initial analysis of some of the proteins properties {e.g., pI, charged residues, modifications (glycosilations), hydrophobicity/hydrophilicity} could lead to specific characteristics to be included in the coating formulation. Analysis of the surface (e.g., energy, roughness, charge, and functional groups) of various packaging components could also lead to specific characteristics and/or modifications of the coating formulation to reduce the adsorption of the protein. With this in mind, preferred coating families are glycols, ethers, esters, alcohols, methacrylates, silanes and derivatized members thereof. Especially preferred coating precursors for use in the present invention include compounds containing carbon-oxygen bonding. Particularly preferred coating precursors include compounds having the elements C, H and O; polyethylene glycols, glycol ethers, commonly known as glymes (e.g., monoglyme, ethyl glyme, diglyme, ethyl diglyme, triglyme, butyl diglyme, tetraglyme, pentaglyme, hexaglyme and their respective corresponding monoalkyl ethers) and functionalized derivatives such as, for example, polyethylene glycol with an end functionalized silane. Coatings applied by this method may be deposited over pre-existing coatings such as barrier coatings (e.g., oxides such as $SiO_2$) and silicone formulations sprayed or dipped and baked on surfaces (i.e. used to provide lubricity for syringes).

Although this application is written preferably in terms of proteins, it can also be applied to other macromolecules or biomolecules such as nucleic acids, peptides, antibodies, polynucleotides (e.g., DNA, RNA, pDNA, etc., oligonucleotides), protein/nucleic acid complexes (e.g., viral particles for gene therapy) in a liquid ("solution") or solid state ("lyophilized"), etc. by straightforward extension. Certain approaches to the methods of the present invention are preferred. For example, the coating may be applied with pulsed electromagnetic radiation, preferably with low or high frequency energy of 40-100 kHz, 13.56 MHz or 2.45 GHz. The coating may be deposited onto the surface of a pharmaceutical package by plasma chemical vapor deposition (CVD), wherein said coating is prepared from a mixture of one or more chemical precursors and an additional carrier gas, such as, an inert gas. Preferable gases include Argon, Helium, Neon, Xenon, Krypton or Nitrogen. The precursor concentration, defined as the ratio total precursor flow/(total carrier gas flow+total precursor flow), is generally between 5% and 95%, preferably between 10% and 90%, and most preferably between 30% and 50%. Pre-conditioning of the substrate by a heat or plasma treatment process before deposition of the coating is desirable. If the substrate temperature is nearly equal to the temperature of the process gas introduced into the reaction chamber, condensation of the process gas on the substrate before, during and after the coating process can be avoided. Thus, it is preferred that the coating is deposited while maintaining an equal or positive temperature difference between the substrate and other parts of the coating system. Typically, the coating is deposited by using an average power density, defined by the ratio average power/plasma volume, between 0.05 $W/cm^3$ and 50 $W/cm^3$. Preferably, the power density is between 0.08 $W/cm^3$ and 10 $W/cm^3$ and most preferably between 0.1 $W/cm^3$ and 5 $W/cm^3$. The coated substrate surfaces may be defined by a fibrinogen adsorption of the coated substrate that is less than 500 $ng/cm^2$, preferably less than 200 $ng/cm^2$ and most preferably less than 150 $ng/cm^2$ (for a $\leqq 10$ μg/ml fibrinogen solution over a incubation period of 72 hours). Coating time may vary depending on the pharmaceutical packaging. Generally, the functional coating that deters macromolecule adsorption onto the surface of a pharmaceutical is deposited in 10 minutes or less, preferably 3 minutes or less, and most preferably 1 minute or less. Coating thickness may also vary. Generally, the functional coating that deters macromolecule adsorption onto the surface of a pharmaceutical package has a coating layer thickness between 0.3 nm and 500 nm, preferably between 0.5 nm and 200 nm, most preferably between 1 nm and 50 nm.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever. The entire disclosure[s] of all patent applications, patents, and papers cited herein are incorporated by reference herein.

EXAMPLES

1) Testing of Generally Accepted Principles for Coatings that Reduce Binding of Proteins Deterring Binding of Positively Charged Proteins.

Proteins such as histone and lysozyme are positively charged at physiological pH (around 7.4) and it is postulated that a positively charged surface should reject the regions of the proteins abundant in positive charges resulting in an overall decrease in the amount of protein adsorbed. Fluorescently labeled histone, human serum albumen, and lysozyme are incubated on a surface that has been coated with an aminosilane (C. G. Panto, E. Metwalli, S. Conzone, D. Haines U.S. Pat. No. 6,916,541 B2). The proteins are incubated at different pH values. A control of bovine serum albumin (BSA) is also included. This protein has an acidic pI (5.2) and would be mostly negatively charged at the pH values tested.

The results shown in FIG. 3 demonstrate the effect of the positively charged surface, where the positively charged proteins (i.e., histone and lysozyme) show a 2-4-fold decrease in adsorption when compared to uncoated glass slides that will have a net negative charge {pI of the aminosilane is around pH 9 (E. Metwalli, D. Haines, O. Becker, S. Conzone, C. Pantano *J. Colloid Interfac. Sci.* 2006, 298, 825-831; U. Jonas, A. del Campo, C. Kruger, G. Glasser, D. Boos *PNAS* 2002, 99, 5034-5039}. The behavior of BSA also agrees with the theoretical considerations of ionic attraction of the negatively charged protein to the amino-coated surface, resulting in an increase in the adsorption to the surface.

2) Testing of Generally Accepted Principles for Coatings that Reduce Binding of Proteins Deterring Protein Adsorption by Various Coatings.

A matrix of proteins and formulations is used to test various coated surfaces. These tests are done on a multiplexed slide (coated and uncoated glass and COC polymer materials) format as disclosed in U.S. Patent Application 60/617,192 titled "Multiplexed protein adsorption assay" where a coated surface is exposed to multiple proteins under different conditions simultaneously. After incubation, the absorbance of proteins to the surface is compared under different conditions, proteins and for different surfaces. The results are then confirmed in the final pharmaceutical package coated with the different coatings.

Fluorescently labeled fibrinogen, insulin, histone, immunoglobulins gamma, and carbonic anhydrase are formulated in 100 mM phosphate at three different pH values (5, 7, and 9). The protein solutions are incubated in different wells on coated and uncoated borosilicate glass slides for a period of 3 days. After the incubation period, the wells are washed and the slides are scanned using a laser fluorimeter to quantify the amount of protein adsorbed. The results are compared to the amounts of protein adsorbed to an uncoated Fiolax control slide (a borosilicate Type 1 glass Schott uses to make pharmaceutical packages).

The results in FIG. 4 describe the average reduction in protein adsorption for all the proteins tested when comparing the performance on the coated slide surface to the control slide surface.

Also indicated is the frequency with which the coatings produced a reduction of at least 50% protein adsorption. Each coating is tested ≧five times with three repeats on each occasion. The coatings and surfaces utilized to obtain the data in FIG. 5 are described below:

1. Fiolax: Glass slide made of type 1 glass composition produced by SCHOTT Form a Vitrum.
2. TG: Tetraglyme (tetraethylene glycol dimethyl ether) coating applied by radio-frequency plasma assisted chemical vapor deposition methods in a batch reactor process. Samples are purchased from the University of Washington Bioengineered Materials Consortium. Coatings are applied as per disclosed in U.S. Pat. Nos. 5,002,794 and 5,153,072.
3. H: A formulation based on an aminosilane and a PEG polymer capped with one NHS-ester applied via spin-coating. The coated slides are purchased from and produced by Accelr8 Corporation according to previously disclosed methods G. Mao, S. W. Metzger, M. J. Lochhead U.S. Pat. No. 6,844,028.
4. SS: A formulation prepared by first depositing poly-L-Lysine onto the surface and then modifying this polymeric surface with PEG groups applied via dip-coating. The binding of the coating is through electrostatic interaction. The coated slides and vials are purchased from and produced by Surface Solutions, GmbH. Zurich, Switzerland.
5. AMC: A multilayer coating combining a metal oxide with fluorinated moieties. The slide coatings (AMC148-18) are provided as free samples, produced by Advanced Materials Components Express LLC (Lamont, Pa.).
6. THF: a perfluoropolyether coating purchased from and produced by Tribofilm Research, Inc. (Raleigh, N.C.) according to the previously disclosed method (V. G. Sakhrani, J. L. Williams, C. Tomasino, P. M. Vernon Jr.—United States Patent Application 2004/0231926).

The results demonstrate that coatings having one or more protein deterring characteristics (non-ionic, sterically shielding, hydrophilic, hydrogen bond accepting, not hydrogen bond donating) reduce the adsorption of proteins to different extents. Coatings with all the protein deterring characteristics demonstrate the highest reduction of protein adsorption, with the tetraglyme producing the largest reduction within the set of protein tested.

3) Protein Adsorption in Pharmaceutical Packaging.

To corroborate the slide based results shown in FIG. 4, a method is developed to quantify the amount of protein adsorbed to the surface of pharmaceutical packaging. The method described in FIG. 5 relies on the removal of the adsorbed protein. Briefly, the fluorescently labeled protein solution is incubated in the pharmaceutical package (PP) for 3 days. The excess is removed and the PP is washed with water for injection three times. The PP is then incubated with 50 mM NaOH supplemented with 0.5% SDS for a period of one hour to remove the adsorbed protein from the surface. After incubation an aliquot is removed and allowed to dry in a well of a multiplexed slide. The wells are then scanned and the fluorescent signal is used to calculate the amount of protein adsorbed. These results can be extrapolated to determine how much total protein is adsorbed.

a) TG and SS coated vials. Fiolax vials are coated with TG (from a batch process) and SS and the adsorption of insulin in these PP is compared to those in Fiolax glass vials (control). The results in FIG. 6 have been normalized to Fiolax and demonstrate that the results seen in the slide assays (FIG. 4) correlate with those seen in PP assays. The tetraglyme coating reduces the adsorption of insulin in a PP by >90% while the SS coating reduces the adsorption by approximately 80%.

b) H coated syringes. Syringes are coated with the H coating solution and tested for the adsorption of insulin. In this case the coating is applied to both glass and polymer (a COC copolymer) syringes and the adsorption is compared to uncoated polymer syringes. The method utilized is the same as that described above and shown in FIG. 5. The results shown in FIG. 7 demonstrate that there is a reduction of protein adsorption of around 90% in the coated syringes when compared to the uncoated control.

4) Variation in Radio-Frequency Plasma Assisted Chemical Vapor Deposition Tetraglyme Coating Uniformity.

Using the method described in Example 2, hydrogel coated slides prepared by spin-coating and tetraglyme coated slides prepared in a batch process by radio-frequency plasma assisted chemical vapor deposition are compared for protein adsorption and coating uniformity. FIG. 8 shows the relative protein adsorption for hydrogel and tetraglyme coatings—tetraglyme coated substrates adsorb less proteins in all 4 tests that had statistical differences between the two coatings. FIG. 9 shows the high variability of the tetraglyme coating macromolecule absorption deterring uniformity compared to the hydrogel coating—coefficient of variation is obtained by dividing the standard deviation by the signal intensity.

5) Deposition of Protein Deterrent Coating wherein Container Acts as Reaction Chamber.

Two Fiolax vials (10 ml total volume) are put into a double chamber reactor and are simultaneously evacuated to a basic pressure below 0.1 mbar. After evacuation of the vials argon flows into the reactor with mass flow rates of 50 sccm at a pressure of 0.2 mbar. The total mass flow is divided into two separate mass flows being nearly the same for each vial. The energy of a pulsed microwave source with a microwave frequency of 2.45 GHz and an average power of 500 Watts is split and coupled into the two separate chambers. A pulsed microwave plasma is ignited inside the two vials and the container is pretreated by the plasma and heated up to a process temperature of 120° C. During a gas exchange time a mixture of tetraethyleneglycoldimethylether gas ("tetraglyme") and argon carrier gas with a tetraglyme concentration of 35% flows into the reactor at a pressure of 0.2 mbar and distributed into the two chambers. The energy of a pulsed microwave source with a frequency of 2.45 GHz and an average power of 5.2 Watts is split and coupled into the two separate chambers. A pulsed microwave plasma is ignited inside the two vials for a duration of 300 seconds and an organic coating with a thickness of about 50 nm is deposited only onto the inner surfaces of the vials. Using a carrier gas in addition to the coating precursor gas reduces or avoids condensation in comparison to a deposition process with only a coating precursor gas.

The fibrinogen adsorption of coated vials and uncoated Fiolax reference vials is tested according to the method presented in FIG. 5. The vials are incubated with 2 ml fibrinogen solution with a fibrinogen concentration of 5 μg/ml containing a phosphate buffer solution with pH 7. In comparison to the uncoated reference samples the amount of adsorbed fibrinogen of the coated vials is reduced by 76%.

6) Comparing Coatings being made from Radio-Frequency Plasma Assisted Chemical Vapor Deposition (Barrel Reactor, Batch Process) vs. Microwave Frequency Plasma Assisted Chemical Vapor Deposition (Article as Reactor, Individual Process).

Tetraglyme coated vials are prepared by radio-frequency plasma assisted chemical vapor deposition in a barrel reactor by a batch process and by microwave frequency plasma assisted chemical vapor deposition using the vial as the reaction chamber as depicted in FIGS. 1*a*-1*c* and 2, and compared for coating uniformity by photoelectron spectroscopy. In particular, the C1s high resolution spectra for batch and individually produced tetraglyme coated vials are compared, showing the higher control of coating uniformity possible by using the article as the reactor. FIG. 10 shows, in tabular form, the carbon/oxygen contribution to the C1s deconvoluted peak from the batch process of two identical batch runs vs. three samples using the article as the chamber. These results clearly indicate higher amounts of the carbon/oxygen contribution are obtained in a more reproducible fashion from the article as the reactor method. The higher percent contribution of the 286.5 peak from the deconvoluted spectrum indicates a higher percent retention of the tetraglyme monomer from the article as the reactor method vs. the batch method.

7) Difference in Deterring Protein Adsorption between Uncoated Control Glass, $SiO_2$ Barrier Coatings Produced by Plasma Impulse Chemical Vapor Deposition, Siliconized Coatings Applied over Control Glass and $SiO_2$ Barrier Coating, and Tetraglyme Coatings Produced by Plasma Assisted Chemical Vapor Deposition.

Using the method described in Example 2 and pictorially shown in FIG. 5 several different coatings are evaluated for their ability to reduce the binding of histone-cy3 and insulin-cy3 in vials. The results shown in FIG. 11 demonstrate the following: 1) control uncoated glass samples strongly adsorb histone-cy3 and insulin-cy3; 2) $SiO_2$ barrier coating ("Type 1+") adsorbs histone-cy3 and fibrinogen-cy3 even more strongly then uncoated control glass; 3) Topas vials adsorb histone-cy3 and insulin-cy3 to a slightly greater extent than uncoated control glass; 4) siliconization of control glass and $SiO_2$ coating do not reduce histone-cy3 and insulin-cy3 adsorption relative to non-siliconized samples; 5) tetraglyme coated vials reduce the adsorbtion of histone-cy3 and insulin-cy3 by a factor of 10.

8) Protein Stability Due to Coatings.

The effect of the glass surfaces on proteins can be very detrimental. The adsorption of proteins through ionic interaction can lead to protein denaturation and loss of activity. Some coatings can also more strongly bind proteins (even through covalent linkages), which can have an immediate effect on the proteins activity. To demonstrate the importance of the inertness of the coating, enzymes are deposited on aldehydesilane, epoxysilane, and H coated Type 1 glass slides and allowed to immobilize for two hours. After that time the activity of the enzymes is determined. As can be observed in FIG. 12, the alkaline phosphatase immobilized onto aldehyde or epoxy coated surfaces have lost all of their activity, while the enzyme immobilized to the H coated surface retains almost all of the activity, indicating that the enzyme is still active.

9) Plasma Deposition Method Necessary for Deterring Protein Adsorption.

Cyclic olefin copolymer microscope slides are coated with tetraglyme from a radio frequency plasma assisted chemical vapor deposition batch process from a barrel reactor system and their deterrence for fibrinogen binding are compared with Type 1 borosilicate glass microscope slides uncoated and coated with tetraglyme from both dip-coating and chemical vapor deposition processes. The objective of this experiment is to determine the importance of the deposition process on the coating properties. The samples are evaluated for fibrinogen binding by the method disclosed in Example 2 using 5 μg/mL fibrinogen in phosphate buffer at pH 7. The results are shown in FIG. 13. FIG. 13 clearly demonstrates that tetraglyme coatings are effective at reducing the adsorption of fibrinogen when deposited via a plasma-assisted process but not when deposited via dip-coating or chemical vapor deposition methods.

The preceding examples can be repeated with similar success by substituting the generically or specifically described reactants and/or operating conditions of this invention for those used in the preceding examples. From the foregoing description, one skilled in the art can easily ascertain the essential characteristics of this invention and, without departing from the spirit and scope thereof, can make various changes and modifications of the invention to adapt it to various usages and conditions.

We claim:

1. A method of preparing a protein deterrent surface on a pharmaceutical package comprising:
    depositing a polyether coating onto a surface of a pharmaceutical package by plasma chemical vapor deposition wherein said pharmaceutical package acts as a coating chamber,
    wherein the coating is deposited while maintaining a positive temperature difference between the pharmaceutical package and the reaction gas.

2. A method according to claim 1, wherein the pharmaceutical package is sealed via a vacuum pump, the package is evacuated only inside by the vacuum pump, and a process gas is introduced directly into the inside of the package through a gas channel.

3. A method according to claim 1, wherein the pharmaceutical package is a vial, a plastic-coated vial, a syringe, a plastic coated syringe, an ampoule, a plastic coated ampoule, a cartridge, a bottle, a plastic coated bottle, a pouch, a pump, a sprayer, a stopper, a plunger, a cap, a lid, a needle, a stent, a catheter or an implant.

4. A method according to claim 1, wherein the pharmaceutical package comes in contact with a pharmaceutical or biotechnological substance or formulation suitable for therapeutic drug delivery.

5. A method according to claim 1, wherein the pharmaceutical package has a coating to lower the surface energy by ≧5 dynes/cm relative to the uncoated pharmaceutical package.

6. A method according to claim 1, wherein the pharmaceutical package has a barrier coating to which the protein adsorption deterrent coating is applied.

7. A method according to claim 1, wherein the pharmaceutical package is made of glass.

8. A method according to claim 6, wherein the glass is Type 1, Type 2, Type 3, a silicate, a borate, a borosilicate, or a phosphate glass or a soda-lime silicate.

9. A method according to claim 1, wherein the coating is applied over an inorganic oxide layer.

10. A method according to claim 9, wherein the inorganic oxide layer is $SiO_2$ or $TiO_2$.

11. A method according to claim 1, wherein the pharmaceutical package is made of polymeric material.

12. A method according to claim 11, wherein the polymeric material is acrylic, polycarbonate, polyester, polypropylene, polyacetal, polystyrene, polyamide, polyacrylamide, polyimide, polyolefin, cyclic olefin polymer, cyclic olefin copolymer, cyclic olefin resins, cyclic olefin-ethylene copolymer, rubber, an elastomer, a thermosetting polymer or a thermoplastic polymer.

13. A method according to claim 1, wherein two or more of said coatings are applied sequentially.

14. A method according to claim 1, wherein said plasma CVD coating is deposited over an existing coating.

15. A method according to claim 1, wherein the pharmaceutical package is pre-conditioned by a heating or plasma treatment process before deposition of the coating.

16. A method according to claim 1, wherein the coating is deposited while the difference between the temperature of the pharmaceutical package and the temperature of the reaction gas used in the chemical vapor deposition process is substantially held at the same level.

17. A method according to claim 1, wherein the coating is deposited by using a power density between 0.08 $W/cm^3$ and 10 $W/cm^3$.

18. A method according to claim 1, wherein the coating is deposited in 3 minutes or less.

19. A method according to claim 1, wherein the coating has a layer thickness between 0.5 nm and 200 nm.

20. A method according to claim 1, wherein the polyether is tetraethylene glycol dimethyl ether.

21. A method according to claim 1, wherein the polyether is a diglyme, a triglyme, a tetraglyme, a pentaglyme or a hexaglyme.

22. A method according to claim 1, wherein the polyether is a triglyme or pentaglyme.

23. A method of preparing a protein deterrent surface on a pharmaceutical package comprising:
depositing a polyether coating onto a surface of a pharmaceutical package by plasma chemical vapor deposition wherein said pharmaceutical package acts as a coating chamber, wherein the pharmaceutical package is made from a metal or an alloy.

24. A method of preparing a protein deterrent surface on a pharmaceutical package according to claim 23, comprising:
depositing a polyether coating onto a surface of a pharmaceutical package by plasma chemical vapor deposition wherein said pharmaceutical package acts as a coating chamber, and wherein the pharmaceutical package is made from a metal or an alloy, and
wherein the coating is deposited while the difference between the temperature of the pharmaceutical package and the temperature of the reaction gas used in the chemical vapor deposition process is substantially held at the same level, or
wherein the coating is deposited while maintaining a positive temperature difference between the pharmaceutical package and the reaction gas.

25. A method of preparing a protein deterrent surface on a pharmaceutical package comprising:
depositing a polyether coating onto a surface of a pharmaceutical package by plasma chemical vapor deposition wherein said pharmaceutical package acts as a coating chamber and is made of a polymeric material,
wherein the polymeric material is cyclic olefin polymer, cyclic olefin copolymer, cyclic olefin resin or cyclic olefin-ethylene copolymer.

26. A method of preparing a protein deterrent surface on a pharmaceutical package according to claim 25, comprising:
depositing a polyether coating onto a surface of a pharmaceutical package by plasma chemical vapor deposition wherein said pharmaceutical package acts as a coating chamber, wherein the pharmaceutical package is made of a polymeric material,
wherein the polymeric material is cyclic olefin polymer, cyclic olefin copolymer, cyclic olefin resin or cyclic olefin-ethylene copolymer, and
wherein the coating is deposited while the difference between the temperature of the pharmaceutical package and the temperature of the reaction gas used in the chemical vapor deposition process is substantially held at the same level, or
wherein the coating is deposited while maintaining a positive temperature difference between the pharmaceutical package and the reaction gas.

\* \* \* \* \*